United States Patent [19]

Hofmann

[11] Patent Number: 4,460,510

[45] Date of Patent: Jul. 17, 1984

[54] PROCESS FOR ALKOXYCARBONYLATING ALPHA-OLEFINS HAVING A SINGLE BRANCH

[75] Inventor: Peter Hofmann, Marl, Fed. Rep. of Germany

[73] Assignee: Chemische Werke Hüls AG, Marl, Fed. Rep. of Germany

[21] Appl. No.: 376,749

[22] Filed: May 10, 1982

[30] Foreign Application Priority Data

May 30, 1981 [DE] Fed. Rep. of Germany ....... 3121573

[51] Int. Cl.³ .............................................. C11C 3/02
[52] U.S. Cl. .............................. 260/410.9 R; 260/413
[58] Field of Search ................. 260/410.9 C, 410.9 R, 260/413 HC

[56] References Cited

U.S. PATENT DOCUMENTS

| | | | |
|---|---|---|---|
| 3,507,891 | 4/1970 | Hearne | 260/410.9 C |
| 3,644,443 | 2/1972 | Shubkin | 260/413 HC |
| 3,661,957 | 5/1972 | Shubkin | 260/413 HC |
| 3,678,083 | 7/1972 | Dubeck et al. | 260/413 HC |
| 3,694,502 | 9/1972 | Keblys et al. | 260/413 HC |
| 3,935,228 | 1/1976 | Keblys | 260/410.9 C |
| 3,946,055 | 3/1976 | Isa et al. | 260/413 HC |
| 3,980,683 | 9/1976 | Isa et al. | 260/413 HC X |

Primary Examiner—Helen M. S. Sneed
Attorney, Agent, or Firm—Wells & Wells

[57] ABSTRACT

A process for reacting alpha-olefins having a single branch of the following general structure:

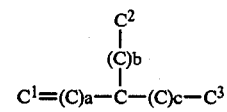

where a,b and c are $7 \leq a+b+c+4 \leq 40$ and where $a \neq b$, $a \neq c$, $a < b$, with carbon monoxide and water or alkanols in the presence of a catalytic system consisting of a cobalt compound and a promoter selected from the group pyridine, a non-ortho-substituted alkylpyridine or a mixture thereof at a pressure of at least 50 bars and at a temperature of 175° to 230° C. into an isomer mixture of carboxylic acids or carboxylic acid alkylesters which is more than 50% acids or esters formed by functionalizing carbon atoms $C^2$ or $C^3$ of the general formula where the reaction is carried out with a promoter to cobalt ratio of 2:1 to 15:1 (atoms of nitrogen to atoms of cobalt) and at olefin conversions exceeding 50%.

11 Claims, No Drawings

PROCESS FOR ALKOXYCARBONYLATING ALPHA-OLEFINS HAVING A SINGLE BRANCH

CROSS-REFERENCE TO RELATED APPLICATIONS

Applicant claims priority under 35 USC 119 for application P 31 21 573.4 filed May 30, 1981 in the Patent Office of the Federal Republic of Germany.

The disclosure of inventor Hofmann's copending application, Ser. No. 125,482, filed Feb. 28, 1980, and now abandoned and U.S. Pat. Nos. 3,883,587 and 3,935,228 cited therein are incorporated herein to show alkoxycarbonylation procedures carried out in the presence of cobalt catalysts and a promotor from the group pyridine, non-ortho-substituted alkylpyridine and mixtures thereof.

BACKGROUND OF THE INVENTION

The field of the invention is the production of alkyl esters of saturated aliphatic carboxylic acids and the present invention is particularly concerned with reacting olefins with carbon monoxide and alkanol in the presence of a catalyst consisting of a cobalt compound and a promoter selected from pyridine, non-ortho-substituted alkylpyridine or mixtures thereof at elevated pressures and elevated temperatures.

The state of the art of such alkoxycarbonylation reactions may be ascertained by reference to U.S. Pat. Nos. 3,507,891, 3,906,016 and 4,041,057 and the article "Hydrocarboxymethylation—an Attractive Route from Olefins to Fatty Acid Esters?" by Peter Hofmann et al as published in I & EC, Product Research & Development, Vol. 19, September 1980, pp. 330–334; the disclosures of which are incorporated herein.

The state of the art of preparing the olefins having a single branch as raw materials for the present invention may be ascertained by reference to German Pat. No. 945,390 and the publication of K. Ziegler et al in Justus Liebigs, ANNALEN DER CHEMIE, Vol. 629, page 121 (1978) the disclosures of which are incorporated herein.

It is known that by reacting olefins with carbon monoxide and a compound having a replaceable hydrogen atom such as an alkanol in the presence of a catalyst containing a metal of Group VIII of the Periodic Table of elements and possibly a promoter, fatty acid esters can be produced as disclosed in J. Falbe, Synthesen mit Kohlenmonoxid, Springer publishers, Berlin, Heidelberg, New York (1967).

This reaction is termed alkoxycarbonylation and is carried out predominantly in the presence of catalysts containing metals of Group VIII of the periodic table of elements. Nickel and cobalt have been found particularly well suited as these catalysts. The catalytic effectiveness of these metals can be further enhanced by adding promoters. Thus the activity and selectivity of cobalt acting as a alkoxycarbonylation catalyst can be substantially improved in the presence of pyridine or derivatives of pyridine, especially non-ortho-substituted alkyl pyridines.

The alkoxycarbonylation of linear olefins that is catalyzed with cobalt/pyridine, cobalt/alkylpyridine or cobalt/mixtures is characterized further by the fact that regardless of the location of the double bond of the initial olefin, reaction products of high linearity, that is with only a slight proportion of branched isomers are always obtained as disclosed in U.S. Pat. No. 3,507,891 and U.S. Patent application Ser. No. 125,482.

Regardless of the selection of the catalytic system, branched reaction products are always obtained from the alkoxycarbonylation of branched olefins. Only scant information is provided by the literature about the distribution and structure of the alkoxycarbonylation products to be expected. Thus Reppe & Kroeper report in Justus Liebigs, ANNALEN DER CHEMIE, Vol. 582, pages 38–71 for instance that when carboxylating 2-ethylhexene-(1), only those two isomers are formed which can be derived by the apposition of H and COOH to the original double bond, i.e. 3-ethylheptanoic acid and 2.2-methylethylhexanoic acid.

When alkoxycarbonylation products or their derivatives are used for instance as surfactants, softeners and lubricants, it is frequently desirable to produce isomer mixtures of another composition in order to affect the properties of application of these products in a controlled manner.

There is a prior art limitation in developing a process permitting the reaction between singly branched alpha-olefins with carbon monoxide and water or alkanols in the presence of a catalytic system consisting of a cobalt compound and a promoter from the group pyridine, a non-ortho-substituted alkylpyridine or a mixture thereof at a pressure of at least 50 bars and at an elevated temperature so that an isomer mixture of carboxylic acids or carboxylic acid alkyl esters is formed that consists in more than 50% of acids or esters obtained by functionalizing those terminal carbon atoms of the initial olefin which originally were not linked by a double C═C with the neighboring carbon atom.

SUMMARY OF THE INVENTION

Having in mind the limitations of the prior art it is an object of the present invention to react alpha-olefins having a single branch with carbon monoxide and water or alkanols in the presence of a catalytic system consisting of a cobalt compound and a promoter selected from the group consisting of pyridine, a non-ortho-substituted alkylpyridine or mixtures thereof at a pressure of at least 50 bars and at an elevated temperature of 175° to 230° into an isomer mixture of carboxylic acids or carboxylic acid alkylesters which is more than 50% acids or esters formed by functionalizing an end position carbon atom of the initial olefin, where the promoter to cobalt ratio is 2:1 to 15:1 (atoms of nitrogen to atoms of cobalt) and the olefin conversion exceeds 50%.

The alpha-olefins having a single branch useful as the starting material in the present invention having the following general formula:

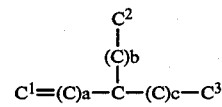

where a,b and c are 7 less than or equal to $a+b+c+4$ less than or equal to 40, and where $a \neq b$, $a \neq c$, a is less than b. The preferred olefins are those for which $a=0$, $b=1,3,5,7,9,11,13,15$ or 17 and $c=b+2$.

The functionalized carbon end groups of the initial olefin are $C^2$ or $C^3$.

Alpha-olefins of this type having a single branch as a rule are prepared by homodimerizing butenes or higher homologues of butene, though they can also be obtained by codimerizing propylene and butenes or higher homologues of these olefins. The various procedures for preparation differ most of all by the catalytic system used in their preparation. Conventional catalysts are aluminum alkyls as disclosed in German Pat. No. 945 390 and the publication of K. Ziegler et al in Justus Liebigs, ANNANLEN DER CHEMIE, Vol. 629, page 121 (1960) or combinations of aluminum alkylene and nickel as disclosed by K. Weissermel, H. J. Arpe, in Industrielle Organische Chemie, Chemie publishers, Weinheim, N.Y., (1978) at p 80. In addition to these procedures wherein the structure of the olefin having a single branch consists of smaller olefinic building blocks, there are obviously also other procedures based on an already existing C structure and wherein the double bond is produced for instance by splitting off hydrogen halides or $H_2O$.

Typically representative olefins having a single branch are for instance: 2-ethylpentene-(1), 2-ethylhexene-(1), 2-ethylheptene-(1), 2-butyloctene-(1), 2-hexyldecene-(1), 2-octyldodecene-(1), 2-hexadecyleicosene-(1) and 3-propylhexene-(1).

All the olefins used in the process of the present invention can be introduced in the pure form or as mixtures with other olefins of the same type or together with paraffins or other inert solvents.

The carbon monoxide used is obtained by known separation methods e.g. low-temperature distillation and molecular sieve separation from synthesis gas. The carbon monoxide preparation procedure does not require removing the hydrogen quantitatively because a hydrogen content not exceeding about 10% by volume is known from experience to favorably affect the rate of reaction in the present invention. On the other hand, all the contaminants degrading the activity of the catalytic system must be removed to the extent required and/or possible.

Water or alkanols are used as further reagents in the process of the present invention. All primary and secondary alkanols having a hydroxyl function are applicable. The preferred alkanols are those having a C number up to and including 4, that is, methanol, ethanol, propanol, isopropanol, n-butanol, iso-butanol, and butanol-2. Provided the processing of the reaction mixture does not demand a higher alkanol, methanol is the preferred esterification component.

The amount of water or alkanol used as a reagent is not critical. Referred to the olefin, less than 1 mole of water or alkanol can be used and the maximum achievable olefin conversion is then limited by the quantity of the co-reagent. As a rule proportions of water or alkanol of 1 to 10 moles per mole of olefin are used.

The catalyst used consists of a cobalt compound and a promoter. Suitable cobalt compounds are carbonyls such as dicobaltoctacarbonyl, carboxylic acid salts such as acetate, naphthenate, 2-ethylhexanoate, laurate and stearate and furthermore carbonates and oxides. The cobalt may be present in all valences possible in these compounds. As a rule the cobalt concentration amounts to about 0.001 to 0.2, preferably 0.01 to 0.08 gram-atoms of cobalt per mole of olefin.

Suitable promoters are pyridine and all non-ortho-substituted halogen-free pyridine derivatives such as beta- and gamma-picoline, 3,4- and 3,5- lutidine and beta- and gamma-ethylpyridine.

The combination of the following reaction conditions is critical for the process of the present invention: temperature, ratio of promoter to cobalt (nitrogen atoms to cobalt atoms) and olefin conversion.

The temperature of reaction must be in the range from 175° to 230° C., preferably from 180° to 200° C. The promoter/cobalt ratio must be in the range from 2:1 to 15:1 nitrogen atoms/cobalt atoms, preferably 7:1 to 12:1. The olefin conversion must be greater than 50%.

Only by observing these critical conditions is it possible to prepare in surprising manner from the olefin starting material the predominantly found isomers having the following general formula:

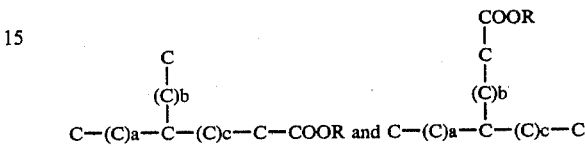

where R=H or alkyl.

It has been found advantageous to select also a specific pressure range in addition to the above cited process-critical conditions of reaction. Appropriate pressures used are less than 250 bars, preferably between about 100 and 200 bars.

In general the process of the present invention is carried out so that the olefin together with the water or alkanol, the promoter and the cobalt compound are placed in an agitator-equipped autoclave and oxygen is removed by scrubbing with an inert gas. After the desired temperature of reaction has been set, carbon monoxide is applied. Due to an automatically controlled internal cooling system and by repeated application of carbon monoxide both the temperature and the pressure are kept constant. When a carbonyl is used as the cobalt compound, it is recommended to apply a carbon monoxide pressure ensuring the stability of the carbonyl during the heating phase. The reaction can be monitored by chromatographic analysis of samples taken during the reaction. When the desired conversion has been reached, the reaction is terminated after cooling the autoclave contents and ensuing decompression.

Upon completion of the reaction, the reaction mixture can be treated at a temperature of 20 to 100, preferably 40° to 60° C. with an oxygenated gas until cobalt compounds, which in the distillation processing lead to the separation of the metallic cobalt have been destroyed by oxidation. This treatment can be carried out for instance in a scrubbing tower by moving the gas countercurrent to the reaction discharge. The oxidative destruction is very easily noted by the discoloration i.e. from brown-orange to blue-violet.

Following the treatment with an oxygenated gas, the reaction discharge is processed by distillation. This procedure may be carried out either by first separating unconverted water or alkanol and olefin as well as promoter and reaction products from the cobalt residue and then carrying out a fractionated distillation, or the fractionated distillation is performed without prior separation of the cobalt compounds. The water or alkanol, olefin, promoter and cobalt residue can be fed back into the conversion process of the present invention.

The process of the present invention can be carried out both in discontinuous and continuous manner. It is frequently appropriate as regards the continous procedure to preform the catalyst. This is done for instance in such a way that the cobalt compound soluble in pyriine or in pyridine derivatives is treated at elevated temperature i.e. 120° to 200° C. and at elevated pressure i.e. 100 to 300 bars for at least 5 minutes with hydrogenated carbon monoxide i.e. 1 to 60% by volume of $H_2$. The cobalt compound furthermore may be the cobalt residue obtained by the distillation processing of a alkoxycarbonylation mixture. The preformed catalyst is used together with olefin and water or alkanol in the alkoxycarbonylation stage.

The carboxylic acids and the alkylesters of saturated aliphatic carboylic acids prepared by the process of the present invention are predominantly used as raw materials in the production of alcohols, carboxylic acids, carboxylic amines and their derivatives. Alcohols are obtained from the products of the present invention by hydrogenation on copper chromite catalysts, carboxylic acids are obtained from the esters by hydrolysis and amines are obtained by reacting the carboxylic acids or esters with ammonia followed by hydrogenation. These products and their derivatives are used for instance as raw materials for detergents, lubrication oil ingredients, emulsifiers and softeners.

Unless explicitly stated otherwise, all percentages in the specific examples below which more comprehensively explain the process of the present invention, are percentages by weight or by mole.

EXAMPLE 1

1 mole of 2-ethylhexene-(1), 2 moles of methanol, 0.03 gram-atom of cobalt in the form a cobalt laurate containing 10% of cobalt and 0.3 moles of gamma-picoline are placed into a stainless steel autoclave. Following heating to 185° C., $H_2$ is first applied through a metering vessel at 2.5 bars, whereupon carbon monoxide (CO) is applied to raise the total pressure to 180 bars, which by repeated applications of CO is kept constant within +/−3 bars. The reaction monitored by chromatography on reaction mixture samples is terminated after 3 hours at an olefin conversion of 90%. The selectivity with respect to nonanoic acid methyl esters is 98%. 49.5% of these esters are 4-methyloctanoic acid methylester, 27% are 6-methyloctanoic acid methylester and 18.5% are 3-ethylheptanoic acid methylester.

EXAMPLE 2

Example 1 is repeated except that 2-hexyldecene-(1) is used in lieu of 2-ethylhexene-(1). After 4.5 hours and an olefin conversion of 87%, the reaction is terminated. The selectivity with respect to heptadecanoic acid methylesters is 95%. 35% of these esters are 8-methylhexadecanoic acid methylester, 33% are 10-methylhexadecanoic acid methylester, and 18% are 3-hexylundecanoic acid methylester.

EXAMPLE 3

1 mole of 2-octyldodecene-(1), 2 moles of methanol, 0.04 gram-atom of cobalt in the form of a cobalt naphthenate containing 10% of cobalt and 0.45 moles of pyridine are placed in the apparatus of example 1. After heating to 190° C., $H_2$ at 2.5 bars is applied first through a metering vessel, and thereupon carbon monoxide is applied for a total pressure of 200 bars which is kept constant within +/−3 bars by repeated application of CO. The reaction monitored chromatographically on removed samples is terminated after 6 hours at an olefin conversion of 92%. The selectivity regarding heneicosanic acid methylesters is 96%. 35% of these esters are 10-methyleicosanic acid methylester, 35% are 12-methyleicosanic acid methylester and 18% are 3-octyltridecanoic acid methylester.

I claim:

1. A process for reacting alpha-olefins having a single branch of the general formula:

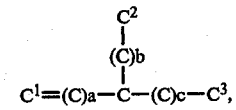

$C^1=(C)_a-C-(C)_c-C^3$, where a, b, and c are $7 \leq$, $a+b+c+4 \leq 40$, and where $a \neq b$, $a \neq c$, $a < b$, with carbon monoxide and a compound having a hydroxyl function selected from the group consisting of water and alkanols in the presence of a catalytic system consisting of a cobalt compound and a promoter selected from the group consisting of pyridine, a non-ortho-substituted alkylpyridine or a mixture thereof at a pressure of at least 50 bars and at a temperature between 175° and 230° C. into an isomer mixture selected from the group consisting of carboxylic acids and carboxylic acid alkylesters formed by functionalizing carbon atoms $C^2$ or $C^3$ of the general formula and carrying out the reaction with a ratio of promoter to cobalt based on atoms of nitrogen to atoms of cobalt of 2:1 to 15:1 and at an olefin conversion exceeding 50%.

2. The process of claim 1, wherein said reaction is carried out at pressures less than 250 bars.

3. A process for reacting alpha-olefins having a single branch of the general formula

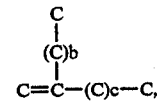

wherein b=1, 3, 5, 7, 9, 11, 13, 15, or 17, and c=b+2, with carbon monoxide and water in the presence of a catalytic system consisting of a cobalt compound and a promoter selected from the group consisting of pyridine, a non-ortho-substituted alkylpyridine or a mixture thereof at a pressure of at least 50 bars and less than 250 bars and at a temperature between 175° and 230° C. into an isomer mixture of carboxylic acids having the general formula:

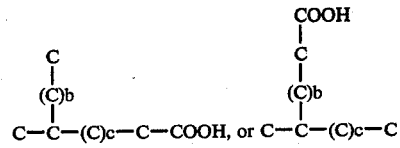

wherein b and c are the same as above, and carrying out the reaction with a ratio of promoter to cobalt based on atoms of nitrogen to atoms of cobalt of 2:1 to 15:1 and at an olefin conversion exceeding 50%.

4. A process for reacting alpha-olefins having a single branch of the general formula:

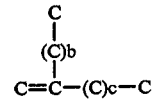

wherein b=1, 3, 5, 7, 9, 11, 13, 15, and 17, and c−b+2, with carbon monoxide and alkanol in the presence of a catalytic system consisting of a cobalt compound and a promoter selected from the group consisting of pyridine, a non-ortho-substituted alkylpyridine or a mixture thereof at a pressure of at least 50 bars and less than 250 bars and at a temperature between 175° to 230° C. into an isomer mixture of carboxylic acid alkylesters having the general formula:

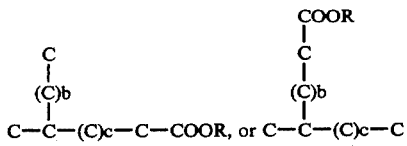

wherein b and c are the same as above and R=alkyl, and carrying out the reaction with a ratio of promoter to cobalt based on atoms of nitrogen to atoms of cobalt of 2:1 to 15:1 and at an olefin conversion exceeding 50%.

5. The process of claim 3, wherein said alpha-olefins are selected from the group consisting of 2-ethylpentene-(1), 2-ethylhexene-(1), 2-ethylheptene-(1), 2-butyloctene-(1), 2-hexyldecene-(1), 2-octyldodecene-(1), 2-hexadecyleicoses-(1), and 3-propylhexene-(1).

6. The process of claim 4, wherein said alpha-olefins are selected from the group consisting of 2-ethylpentene-(1), 2-ethylhexene-(1), 2-ethylheptene-(1), 2-butyloctene-(1), 2-hexyldecene-(1), 2-octyldodecene-(1), 2-hexadecyleicoses-(1) and 3-propylhexene-(1).

7. The process of claim 3, wherein said temperature of reaction is 180° to 200° C.

8. The process of claim 4, wherein said temperature of reaction is 180° to 200° C.

9. The process of claim 7, wherein said ratio of promoter to cobalt is 7:1 to 12:1.

10. The process of claim 8, wherein said ratio of promoter to cobalt is 7:1 to 12:1.

11. The process of claim 6, wherein said alkanol is selected from the group consisting of methanol, ethanol, propanol, isopropanol, n-butanol, iso-butanol, and butanol-2.

* * * * *